United States Patent
Huber et al.

(10) Patent No.: US 7,265,197 B2
(45) Date of Patent: Sep. 4, 2007

(54) POLYMERIC DISPERSANT

(75) Inventors: Gregory T. Huber, Indian Springs, OH (US); Niranjan Deo, Mason, OH (US); Paul A. Merchak, Loveland, OH (US); Terence R. Chamberlain, Montgomery, OH (US); Russell J. Schwartz, Cincinati, OH (US)

(73) Assignee: Sun Chemical Corporation, Parsippany, NJ (US)

( * ) Notice: Subject to any disclaimer, the term of this patent is extended or adjusted under 35 U.S.C. 154(b) by 583 days.

(21) Appl. No.: 10/730,212

(22) Filed: Dec. 5, 2003

(65) Prior Publication Data
US 2005/0120911 A1 Jun. 9, 2005

(51) Int. Cl.
C08G 69/26 (2006.01)
C08L 77/06 (2006.01)
C09D 11/10 (2006.01)

(52) U.S. Cl. ............ 528/350; 523/160; 524/600
(58) Field of Classification Search ............ 523/160, 523/161
See application file for complete search history.

(56) References Cited

U.S. PATENT DOCUMENTS

| 4,496,686 A | 1/1985 | Ansel | 524/850 |
|---|---|---|---|
| 4,661,582 A | 4/1987 | McCready | 528/292 |
| 4,673,705 A | 6/1987 | Ansel et al. | 524/850 |
| 4,754,056 A | 6/1988 | Ansel et al. | 560/171 |
| 5,021,544 A * | 6/1991 | Padget et al. | 528/272 |
| 5,034,444 A * | 7/1991 | Yun et al. | 524/223 |
| 5,180,802 A * | 1/1993 | Hartman et al. | 528/335 |
| 5,239,048 A * | 8/1993 | Speranza et al. | 528/340 |
| 5,286,873 A | 2/1994 | Cook | 548/522 |
| 5,540,851 A | 7/1996 | Lange | 508/194 |
| 5,576,416 A * | 11/1996 | Walker | 528/340 |
| 5,688,312 A | 11/1997 | Sacripante et al. | 106/31.49 |
| 5,747,562 A * | 5/1998 | Mahmud et al. | 523/215 |
| 6,037,414 A | 3/2000 | Simms et al. | 525/176 |
| 6,110,264 A | 8/2000 | Banning et al. | 106/31.29 |
| 6,114,430 A * | 9/2000 | Paulson et al. | 524/432 |
| 6,429,266 B2 * | 8/2002 | Vickers et al. | 525/420 |

* cited by examiner

Primary Examiner—Callie Shosho
(74) Attorney, Agent, or Firm—Dickstein Shapiro LLP

(57) ABSTRACT

A polymeric dispersant of the structure:

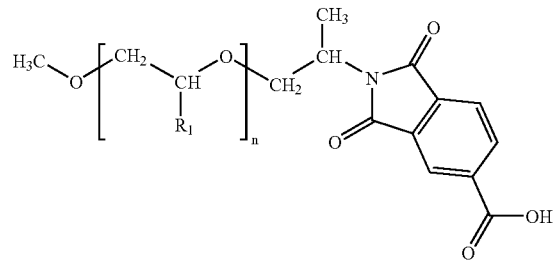

wherein $R_1$ is selected from the group consisting of H, $CH_3$, and a combination thereof, and n is an integer from 4 to 200, for use in printing inks.

13 Claims, No Drawings

POLYMERIC DISPERSANT

FIELD OF THE INVENTION

The invention relates to a polymeric dispersant for use in printing inks.

BACKGROUND OF THE INVENTION

It is most desirable for printers, for example those employing energy curable (e.g., ultra violet or electron beam curable), to generate printed products with the highest resolution and quality. However, numerous problems ensue when attempting to provide high resolution in that the printing quality suffers. The major problem in printing at high resolution is ensuring that each drop of printed ink contains enough pigment to produce a bright vibrant color. Simply loading more pigment to the printing ink causes other defects that adversely affect its quality, such as the occurrence of unwanted high viscosity and poor printing quality. Incorporation of known dispersants help to neutralize some defects but they do not provide for low viscosity, high gloss and high print quality.

U.S. Pat. No. 6,110,264 discloses a phase change ink composition where one component is an anhydride/alcohol or amine inclusive product. Mixed reaction products include carboxylic acid/amide/imide/ester as carriers only and only for use in phase change ink jet systems. U.S. Pat. No. 6,037,414 describes a graft polymer composed of an acrylic polymer backbone and pending from it polyester side chains, cyclic imides, and quaternary ammonium groups. The polymers result in compatibility problems and therefore printing quality problems. U.S. Pat. No. 5,688,312 discloses a hot melt ink composition that contains molecules possessing imide or bisimide groups. The imides are obtained by the reaction of a polyoxyalkylene amine with various phthalic anhydride or succinic anhydride derivatives. The molecular structure of these dispersants does not contain any free carboxylic acid groups which is required to properly bond the dispersant to the laked pigments. U.S. Pat. No. 5,286,873 discloses an imide-linked polymer dispersant for lubricating oils obtained by reacting polyisobutylene anhydride with a polyoxyalkylene amine for use in eliminating piston varnish and sludge in an internal combustion engine. U.S. Pat. Nos. 4,754,056 and 4,673,705 both describe an ultra-violet curable polymeric dispersant possessing acrylate functional groups in the backbone. Also, the polymer possesses free carboxyl groups that assist in wetting the pigment and in stabilizing the dispersion. However, the dispersant is not compatible with solvent systems and also has printing quality problems. U.S. Pat. No. 4,496,686 discloses a dispersant obtained by reaction of a polycarboxylic acid anhydride having a molecular weight of 100-4000 with an alcohol or a primary amine, forming the corresponding half ester or half amide respectively. The dispersant is used in radiation-curable inks and coatings but has printing quality problems.

Thus, there exists a need for an appropriate dispersant for use in formulating printing inks which provides for more efficient wetting and deflocculation of the pigment, affording a more stable dispersion and thereby providing high print quality such as high gloss and low viscosity.

SUMMARY OF THE INVENTION

It has now been found that the above objectives can be realized by printing ink formulations employing a polymeric dispersant of the following structure:

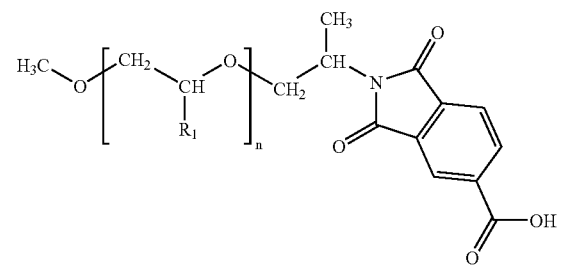

wherein $R_1$ is a hydrogen or a methyl group or combination thereof and number average value of n is an integer from 4 to 200.

The present invention also provides a method of preparing the polymeric dispersant comprising reacting a polyoxyalkene amine with 1,2,4-benzenetricarboxylic acid anhydride.

The present invention further provides a method of reducing the viscosity and improving the gloss of a printing ink composition comprising adding to said ink composition the polymeric dispersant of the present invention.

Other objects and advantages of the present invention will become apparent from the following description and appended claims.

DETAILED DESCRIPTION OF THE INVENTION

It has been surprisingly discovered that a polymeric dispersant of the structure:

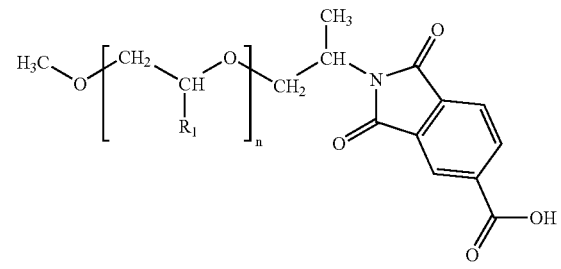

wherein $R_1$ is a hydrogen, a methyl group or combination thereof, n is an integer from 4 to 200. The polymeric dispersant provides reduced viscosity and increased gloss when used to formulate printing ink compositions.

Preferably, n is from 20 to 65, more preferably 35. Also preferably, the average molecular weight of the polymeric dispersant is from about 1,000 to about 10,000, more preferably from about 1,000 to about 3,000 and most preferably about 2,200.

The polymeric dispersant of the present invention provides improved viscosity and gloss for printing inks and coatings and cosmetic applications, which contain high concentrations of laked pigments. Laked pigments as used herein are precipitated salts of pigments containing sulfonic acid and/or carboxylic acid groups precipitated with an alkaline-earth metal or manganese. In high concentrations laked pigments can affect viscosity, gloss and stability of the printing inks and dispersions. Laked pigments include, but are not limited to, the following pigments: Beta Napthol Pigment Lakes such as Pigment Red 49 (Red 49:1 and Red 49:2), Red 50:1, Red 51, Red 53 (Red 53:1 and Red 53:3), Red 68, Orange 16, Orange 17:1, Orange 46; BONA Pigment Lakes such as Red 48:1, Red 48:2, Red 48:3, Red 48:4, Red 48:5, Red 52:1, Red 52:2, Red 57:1, Red 58:2, Red 58:4, Red 63:1, Red 63:2, Red 64, Red 64:1, Red 200, Brown 5; Napthol AS Pigment Lakes such as Red 151, Red 237, Red 239, Red 240, Red 243, Red 247, Naphthalene Sulfonic Acid Pigment Lakes such as Yellow 104, Orange 19, Red 60, Red 66, Red 67.

The polymeric dispersant can be prepared, for example, by reacting a polyoxyalkene amine with 1,2,4-benzenetricarboxylic acid anhydride. The polymeric dispersant is formulated in a one-pot reaction. A polyoxyalkene amine is treated with a 1,2,4-benzenetricarboxylic acid anhydride. The polyoxyalkene amine may be a copolymer of polyethylene oxide and polypropylene oxide, preferability is based on the particular type of printing ink system being employed. The reaction is carried out at a temperature of at least 90° C. The mixture of a polyoxyalkene amine and 1,2,4-benzenetricarboxylic acid anhydride is stirred continuously and heated for between 30 minutes and 10 hours, more preferably at 2 hours, at a temperature of about 100° C. to about 180° C., and most preferably at a temperature of up to 120° C. The temperature of the mixture is then raised up to 220° C., but more preferably about 160° C., and maintained at this temperature for about one hour, up to 10 hours. The mixture is then allowed to slowly cool to room temperature.

The polymeric dispersant is added to an application system which may be a solvent based, water based, energy curable system (ultra-violet, electron beam or cationic) or combination of those systems. The application system contains a laked pigment.

There are many advantages in using the polymeric dispersant of the present invention. It is produced in a simple one-pot reaction and therefore its manufacture is economical and streamlined. It can be used in a variety of printing ink systems such as solvent based, water based and energy curable printing ink systems or combinations of those ink systems. Further, the polymeric dispersant has excellent properties for lowering the viscosity of printing ink systems while maintaining high print quality and resolution. In addition, due to it being a liquid, it is easy to dispense and does not exhibit dusting problems.

The polymeric dispersant of the present invention is further illustrated by the following non-limiting examples in which all parts and percentages of components are by weight and based on the total weight of the composition, unless otherwise indicated.

EXAMPLE 1

Polyoxyalkene amine (200 parts, XTJ-507 from Huntsman Chemicals Austin, Tex.) was mixed and stirred with liquid amine 1,2,4-benzenetricarboxylic anhydride (20.1 parts, from Aldrich Chemical Company of Milwaukee, Wisconsin) and heated to 120° C. for about 2 hours while the solid reactant slowly dissolved. The temperature of the mixture was raised to 160° C., maintained for one hour and then cooled slowly to room temperature. The reaction product was a golden yellow liquid having a viscosity of 1990 cPs (measured by Brookfield viscometer spindle #3 at room temperature), an amine number of 0, and acid number of 29.4.

EXAMPLE 2

Two Ultra Violet Curable printing inks were formulated; one using the polymeric dispersant of Example 1 (Ink 2A) and the other without a dispersant (Ink 2B). The inks were formulated as set forth in Table 1 below:

TABLE 1

| COMPONENT | INK 2A | INK 2B |
|---|---|---|
| Experimental Dispersant of Example 1 | 2% | 0% |
| Pigment Red 52:1 (Bon Red 218-0640) | 19% | 19% |
| Cyracure 6105 (UV curable ink vehicle) | 44% | 45% |
| Cyracure 6974 (UV initiator) | 2% | 2% |
| Cyracure 6990 (UV initiator) | 2% | 2% |
| Limonene Dioxide | 31% | 32% |
| Viscosity (centipoise at room temperature) | 6220 | 10,000 |
| TOTAL | 100% | 100% |

The inks were tested for viscosity by placing them in a Brookfield viscometer Spindle #4 (manufactured by Brookfield of Middleboro, Mass.) and measured at 60 revolutions per minute and at 23° C.

EXAMPLE 3

Two high pigment content dispersions suitable for use in solvent packaging ink compositions were formulated; one using the polymeric dispersant of Example 1 (Ink 3A) and the other without a dispersant (Ink 3B). The inks were formulated as set forth in Table 2 below:

TABLE 2

| COMPONENT | INK 3A | INK 3B |
|---|---|---|
| Experimental Dispersant of Example 1 | 2 g | 0 |
| Pigment Red 52:1 (Bon Red 218-0640) | 16 g | 16 g |
| 40% Nitrocellulose Resin Ink Vehicle | 28 g | 28 g |
| Isopropyl Acetate | 52 g | 53 g |
| Tall oil Fatty Acid | 1 g | 1 g |
| Epoxidized vegetable oil | 1 g | 1 g |
| TOTAL | 100 g | 100 g |

The inks were then tested for viscosity by placing them first in a Brookfield viscometer Spindle #4 at 12 rpm and second in a Brookfield viscometer Spindle #4 at 30 rpm (both at room temperature or 23° C.). The results are set forth in Table 3 below:

TABLE 3

|  | INK 3A | INK 3B |
|---|---|---|
| Viscosity measured at 12 rmp | 350 centipoise | 500 centipoise |
| Viscosity measured at 30 rmp | 260 centipoise | 340 centipoise |

EXAMPLE 4

Eight UV curable printing inks were formulated using laked pigments (four Bon Reds and four Litho Rubines). The first and fifth printing inks employed the polymeric dispersant of Example 1 (Inks 4A and 4E), the second and sixth printing inks were conventional standard inks without any dispersant (inks 4B and 4F), the third and seventh printing inks were less viscous inks employing the polymeric dispersant of Example 1 (Inks 4C and 4G), and the fourth and eight printing inks were less viscous conventional standard inks without a dispersant (Inks 4D and 4H). The inks were formulated in two stages, the first set forth in Table 4 below:

TABLE 4

| COMPONENT | INK 4A | INK 4B | INK 4C | INK 4D | INK 4E | INK 4F | INK 4G | INK 4H |
|---|---|---|---|---|---|---|---|---|
| Experimental Dispersant of Example 1 | 3% | 0 | 3% | 0 | 3% | 0 | 3% | 0 |
| Pigment Red 52:1 (Bon Red 218-0640) | 20% | 20% | 17% | 17% | 0 | 0 | 0 | 0 |
| Pigment 57:1 (Litho Rubine 219-3707) | 0 | 0 | 0 | 0 | 20% | 20% | 17 | 17% |
| Cyracure 6105 (UV curable ink vehicle) | 77% | 80% | 80% | 83% | 77% | 80% | 80% | 83% |
| TOTAL | 100% | 100% | 100% | 100% | 100% | 100% | 100% | 100% |

The pre-ink components in each case were combined and mixed in the presence of 300 g of ⅛$^{th}$ inch steel shot for thirty minutes. The pre-ink compositions were then strained to remove the steel shots and cooled to room temperature.

The pre-inks were tested for viscosity by placing them in a Brookfield viscometer Spindle #4 (manufactured by Brookfield of Middleboro, Mass.) at 60 revolutions per minute and at 23° C. The results are contained in Table 6 below with the gloss results of the final ink composition.

The pre-inks were formulated to final printing ink composition by adding the components set forth in Table 5 below:

TABLE 5

| COMPONENT | INK 4A | INK 4B | INK 4C | INK 4D | INK 4E | INK 4F | INK 4G | INK 4H |
|---|---|---|---|---|---|---|---|---|
| Pre-Ink composition | 89.4% | 89.4% | 89.4% | 89.4% | 89.4% | 89.4% | 89.4% | 89.4% |
| Limonene Dioxide | 10% | 10% | 10% | 10% | 10% | 10% | 10% | 10% |
| Cyracure 6974 (UV initiator) | .3% | .3% | .3% | .3% | .3% | .3% | .3% | .3% |
| Cyracure 6990 (UV initiator) | .3% | .3% | .3% | .3% | .3% | .3% | .3% | .3% |
| TOTAL | 100% | 100% | 100% | 100% | 100% | 100% | 100% | 100% |

The UV curable printing ink compositions were tested for gloss by making three draw downs of each ink using a #3 Meyer Rod on a black & white morest card and curing the ink using an Ultra Violet lamp (300 wpi, 100 fpm). Gloss was measured using a MicroGloss 60° (from BYK/Gardner USA Laboratories of Columbia, Md.). The results are shown in Table 6 below, along with the viscosity measurements/results of the pre-ink compositions:

TABLE 6

| | INK 4A | INK 4B | INK 4C | INK 4D | INK 4E | INK 4F | INK 4G | INK 4H |
|---|---|---|---|---|---|---|---|---|
| Viscosity measured at 60 rmp | 5300 | 6710 | 3750 | 4973 | 5700 | >10,000 | 4310 | >10,000 |
| Gloss | 92.5 | 83.4 | 94.3 | 84.3 | 95.3 | 77 | 94.6 | 86 |

Accordingly, the addition of a polymeric dispersant in each instance resulted in a significant drop in viscosity for the ink composition while a high printing quality was maintained, as evidenced by higher gloss values.

The invention has been described in terms of preferred embodiments thereof, but is more broadly applicable as will be understood by those skilled in the art. The scope of the invention is only limited by the following claims.

What is claimed is:

1. A polymeric dispersant compound for use in printing inks consisting essentially of the structure:

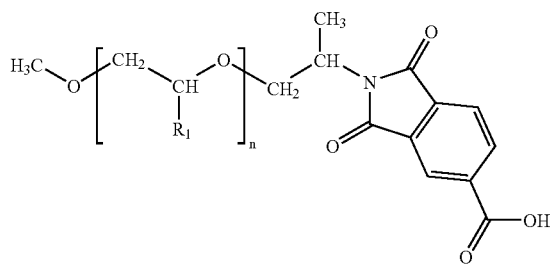

wherein each $R_1$ is individually selected from the group consisting of H and $CH_3$, and n is an integer from 4 to 200.

2. The compound of claim 1, wherein n is an integer from 20 to 65.

3. The compound of claim 2, wherein n is 35.

4. An energy curable printing ink composition containing the compound of claim 1.

5. A solvent based printing ink composition containing the compound of claim 1.

6. A water based printing ink composition containing the compound of claim 1.

7. A method for reducing the viscosity of an energy curable printing ink by adding the compound of claim 1 to the ink.

8. A method for increasing the gloss of an energy curable printing ink by adding the compound of claim 1 to the ink.

9. A polymeric dispersant compound for use in printing inks being the reaction product of reacting a polyoxyalkene amine with 1,2,4-benzenetricarboxylic acid anhydride consisting essentially of the structure:

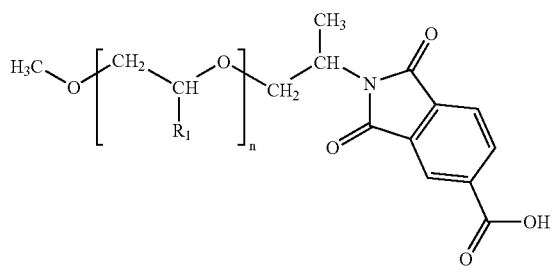

wherein each $R_1$ is individually selected from the group consisting of H and $CH_3$, and n is an integer from 4 to 200.

10. The compound of claim 9 wherein the polyoxyalkene amine is derived from a copolymer of polyethylene oxide and a polypropylene oxide.

11. An energy curable printing ink polymeric dispersant additive of the structure:

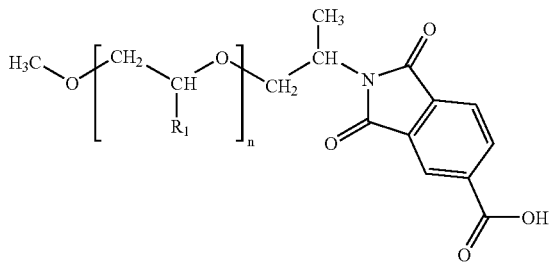

wherein each $R_1$ is individually selected from the group consisting of H and $CH_3$, and n is an integer from 4 to 200.

12. A viscosity reducing printing ink polymeric dispersant additive of the structure:

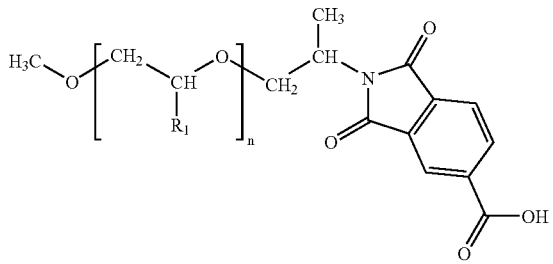

wherein each $R_1$ is individually selected from the group consisting of H and $CH_3$, and n is an integer from 4 to 200.

13. A gloss increasing energy curable printing ink polymeric dispersant additive of the structure:

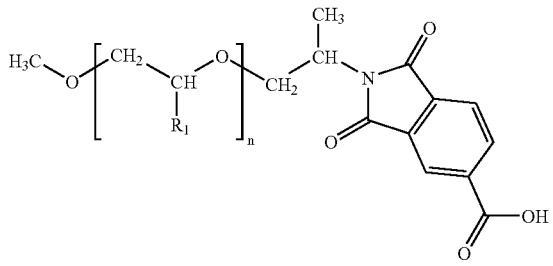

wherein each $R_1$ is individually selected from the group consisting of H and $CH_3$, and n is an integer from 4 to 200.

* * * * *